United States Patent [19]
Hunt et al.

[11] Patent Number: 5,897,833
[45] Date of Patent: Apr. 27, 1999

[54] SYSTEMS AND METHODS FOR DISINFECTING CONTACT LENSES

[75] Inventors: Terrence J. Hunt, Anaheim Hills; Peter G. Bakhit, Huntington Beach, both of Calif.

[73] Assignee: Allergan, Waco, Tex.

[21] Appl. No.: 08/722,718

[22] Filed: Sep. 30, 1996

[51] Int. Cl.⁶ .............................. C12S 9/00; A61K 9/08; C12Q 1/30
[52] U.S. Cl. .............................. 422/28; 422/30; 422/256; 422/292; 222/145.1; 514/839; 514/840
[58] Field of Search ............................. 422/28, 30, 256, 422/292; 210/632; 222/145.1; 514/839, 840

[56] References Cited

U.S. PATENT DOCUMENTS

| | | | |
|---|---|---|---|
| Re. 32,671 | 5/1988 | Huth et al. | 252/95 |
| 2,941,696 | 6/1960 | Homm | 222/136 |
| 3,197,071 | 7/1965 | Kuster | 222/94 |
| 3,200,995 | 8/1965 | Gangwisch | 222/94 |
| 3,760,986 | 9/1973 | Castner et al. | 222/137 |
| 4,476,108 | 10/1984 | Kessler et al. | 424/50 |
| 4,588,586 | 5/1986 | Kessler et al. | 424/94 |
| 4,674,658 | 6/1987 | Van Brocklin | 222/137 |
| 4,731,192 | 3/1988 | Kenjo et al. | 252/95 |
| 4,748,992 | 6/1988 | Giefer | 134/84 |
| 4,767,559 | 8/1988 | Kruse et al. | 252/106 |
| 4,826,658 | 5/1989 | Kay | 422/30 |
| 4,976,921 | 12/1990 | Itagaki et al. | 422/28 |
| 5,011,661 | 4/1991 | Schafer et al. | 422/30 |
| 5,137,178 | 8/1992 | Stokes et al. | 222/94 |
| 5,336,434 | 8/1994 | Park et al. | 252/187.21 |
| 5,362,647 | 11/1994 | Cook et al. | 435/264 |
| 5,364,601 | 11/1994 | Salpekar | 422/28 |
| 5,366,694 | 11/1994 | Stockel | 422/37 |

FOREIGN PATENT DOCUMENTS

| | | |
|---|---|---|
| 0219220 | 4/1987 | European Pat. Off. . |
| 0381616 | 8/1990 | European Pat. Off. . |
| 9317721 | 9/1993 | WIPO . |
| 9417833 | 8/1994 | WIPO . |
| 9526756 | 10/1995 | WIPO . |

OTHER PUBLICATIONS

DeLuca et al. Incactivation of an animal and a fungal catalase by hydrogen peroxide. Arch. Biochem. Biophys. 1995:129–134, Jun. 1995.

*Primary Examiner*—Elizabeth Kemmerer
*Assistant Examiner*—David S. Romeo
*Attorney, Agent, or Firm*—Frank J. Uxa

[57] ABSTRACT

A system for disinfecting a contact lens includes a first container section holding a first liquid medium containing hydrogen peroxide. A second container section is provided and holds a second liquid medium containing a hydrogen peroxide destroying component. The first and second container sections are configured to substantially simultaneously provide the first liquid medium and the second liquid medium to form a combined liquid medium containing an amount of hydrogen peroxide from the first liquid medium effective to disinfect a contact lens contacted with the combined liquid medium and an amount of hydrogen peroxide destroying component from the second liquid medium effective to destroy at least a major amount of the hydrogen peroxide in the combined liquid medium.

15 Claims, 2 Drawing Sheets

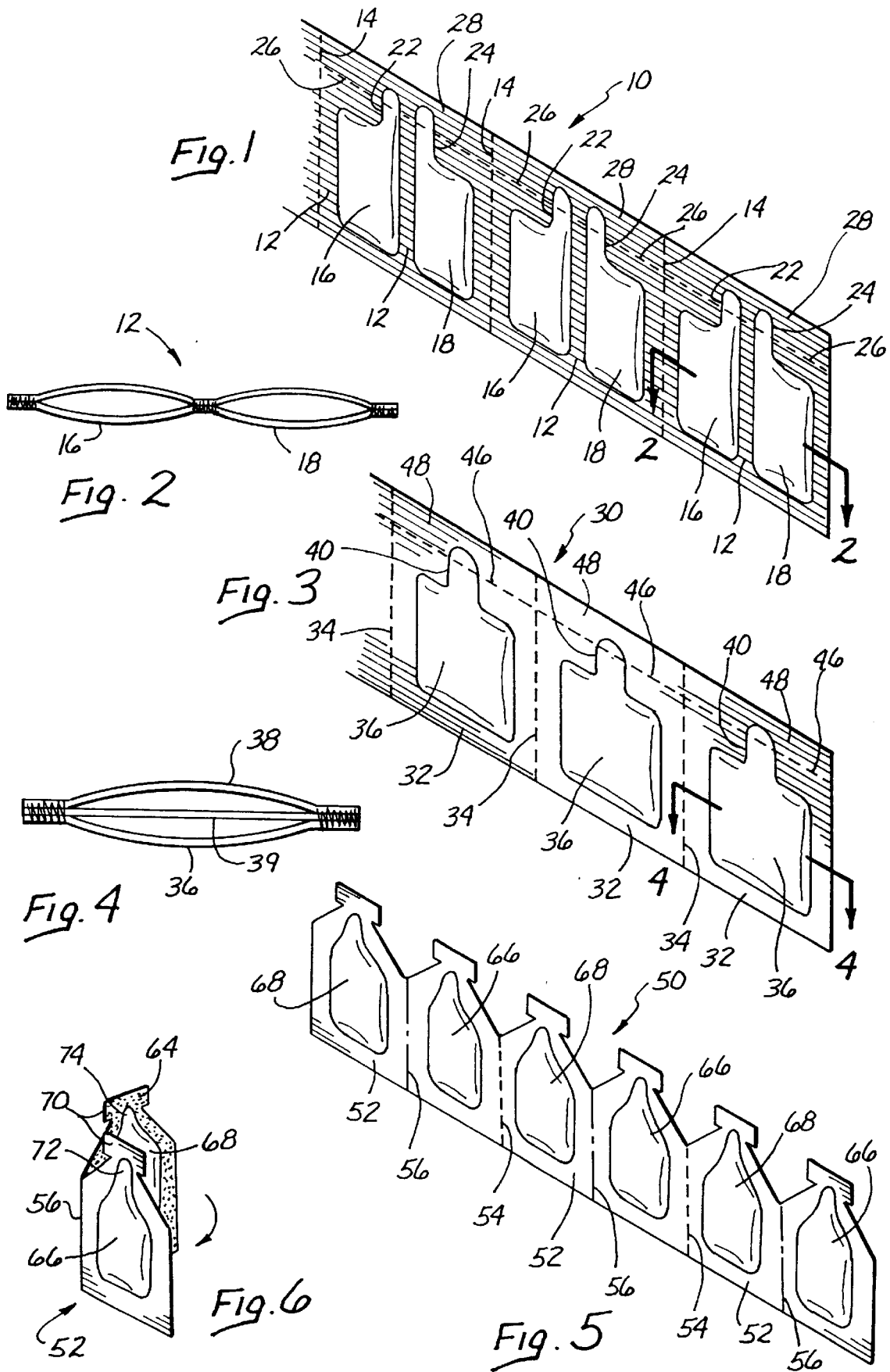

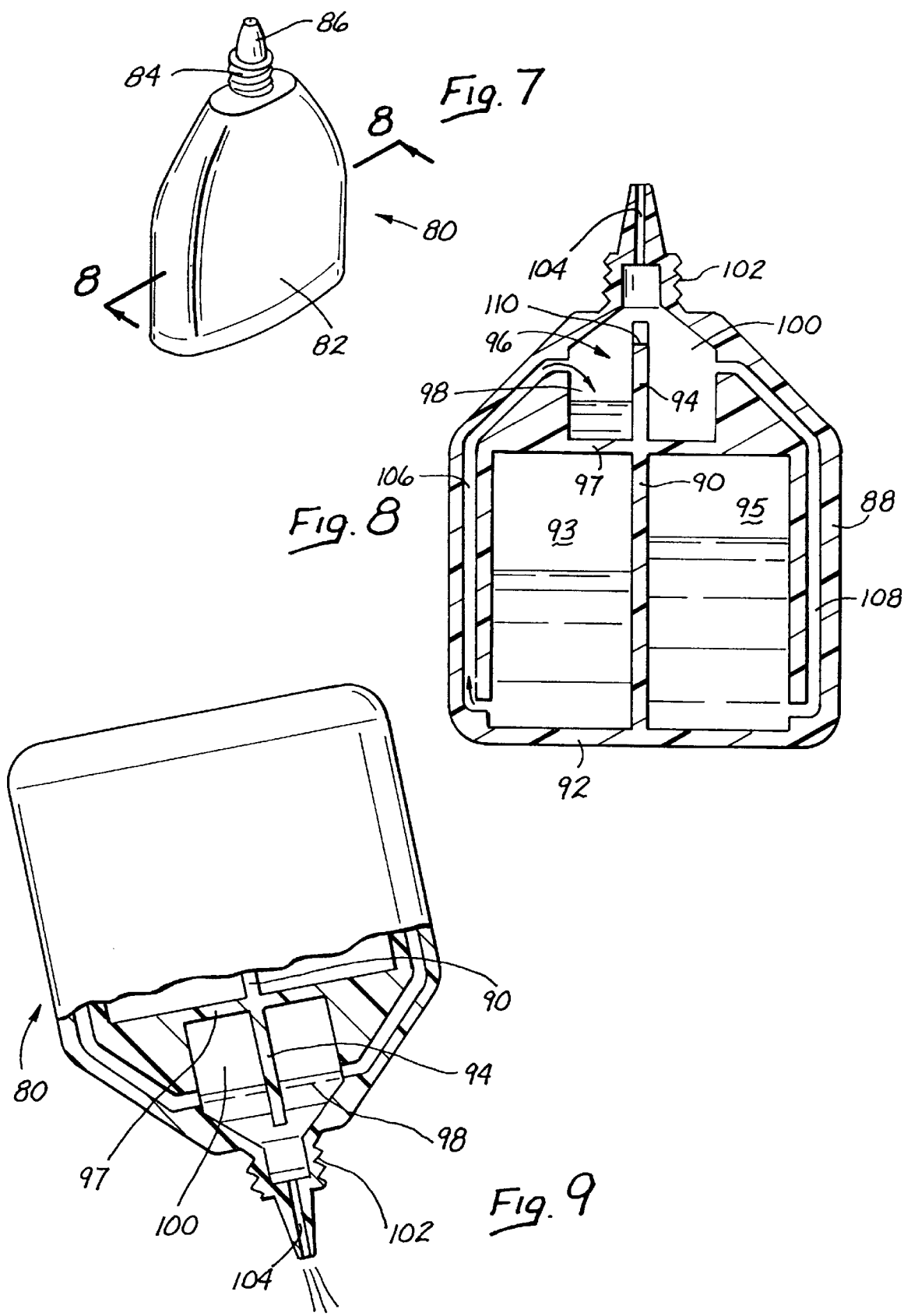

SYSTEMS AND METHODS FOR DISINFECTING CONTACT LENSES

BACKGROUND OF THE INVENTION

This invention relates to systems and methods for disinfecting contact lenses. More particularly, the invention relates to systems and methods adapted to simultaneously combine a disinfectant component and a disinfecting destroying or inactivating component so that a contact lens contacted with this combined material is disinfected and can be placed in the eye of a human being for safe and comfortable wear.

Contact lenses should be periodically disinfected by the user to prevent infection or other deleterious effects on ocular health which may be associated with contact lens wear. Currently, there are several different conventional systems and methods which enable the user to disinfect his/her contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are hydrogen peroxide disinfection systems. Disinfecting hydrogen peroxide solutions are effective to kill the bacteria and fungi which may contaminate contact lenses. However, residual hydrogen peroxide on a disinfected contact lens may cause irritation, burning or trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens. Liquid media (not including the hydrogen peroxide contained therein) used to disinfect contact lenses should be substantially isotonic, for example, to the human eye, and preferably ophthalmically acceptable so as to reduce the chances of problems caused by placing the disinfected lenses in the wearer's eyes.

Thus, there are substantial advantages to destroying hydrogen peroxide before placing the treated lens in one's eye.

Conventional hydrogen peroxide disinfection of a contact lens often involves the use of a hydrogen peroxide destroying component (HPDC), such as platinum, secured to a reusable disc or in a sequential process. Platinum-containing discs can degrade and become ineffective with time and repeated use due to adsorbed tear components and oxidation. This ineffectiveness can result in potentially damaging amounts of hydrogen peroxide being introduced into the eyes.

In a typical sequential process, hydrogen peroxide is first used to disinfect the contact lens. Then, after the contact lens has been disinfected, a HPDC is used to destroy the hydrogen peroxide, For example, after contact lens disinfection in a hydrogen peroxide-containing liquid medium (HPLM), a second liquid medium containing a HPDC is added to the HPLM to destroy the hydrogen peroxide. Alternatively, the HPDC can be included in a tablet or pill having a delayed release coating. After the lens is disinfected in the HPLM, the HPDC is released into the HPLM to destroy the hydrogen peroxide.

Such sequential processes are time consuming and involve either two or more steps or a delayed release coating. The multi-step processes adversely effect user compliance. For example, a lens wearer may forget the step to destroy the hydrogen peroxide and place damaging amounts of hydrogen peroxide in the eye. Delayed release coatings, on the other hand, are often at least partially soluble in the HPLM and can be carried with the disinfected lens when the lens is placed in the eye to be worn. Certain wearers may have an actual or perceived sensitivity to such solubilized coatings in the eye.

Therefore, it would be advantageous to provide contact lens disinfection systems and methods which are effective, involve a single step and/or reduce, or even eliminate, the risk of placing hydrogen peroxide in the eyes.

SUMMARY OF THE INVENTION

New systems and methods for disinfecting contact lenses have been discovered. The present systems and methods provide for effective contact lens disinfection, while enhancing user compliance and reducing the risks of the eye being exposed to hydrogen peroxide. Because the present systems and methods often involve a single user activated step, the user can very easily and effectively employ the present invention to achieve the benefits desired.

In one broad aspect of the present invention, systems for disinfecting a contact lens comprise a first container section holding a first liquid medium containing hydrogen peroxide, and a second container section holding a second liquid medium containing a hydrogen peroxide destroying component (HPDC). Although the container sections may be separate and apart from each other, preferably the first and second container sections are joined together, or may be in a single unit separated by a barrier between the two container sections. The first and second container sections are configured to substantially simultaneously provide the first liquid medium and the second liquid medium to form a combined liquid medium containing an amount of hydrogen peroxide from the first liquid medium effective to disinfect a contact lens contacted with the combined liquid medium. In addition, an amount of HPDC from the second liquid medium is provided and is sufficient to destroy at least a major amount, preferably all, of the hydrogen peroxide in the combined liquid medium.

It has been found that by selecting the proper combination of first and second liquid media, and in particular the amount of hydrogen peroxide and the amount and type of HPDC, both contact lens disinfection and destruction of residual hydrogen peroxide can be achieved in the combined liquid medium and product thereof. Thus, after the hydrogen peroxide has been destroyed, the disinfected contact lens can be removed from the resulting liquid medium, that is from the product of the combined liquid medium, and placed directly in the eye for safe and comfortable wear. As an added safeguard, the user, after taking the lens from the resulting liquid medium, may rinse the lens in saline or other suitable medium before placing the lens in the eye for safe and comfortable wear.

The HPDC is preferably catalase, and more preferably catalase resulting from the action of Aspergillus niger, in an amount from the second liquid medium effective to destroy at least 95% of the hydrogen peroxide originally present in the combined liquid medium. The amount of catalase in the combined liquid medium is preferably controlled so that the contact lens in contact with the combined liquid medium is disinfected before at least 95% of the hydrogen peroxide originally present in the combined liquid medium is destroyed.

The present system can be provided as unit doses, for example, with the first container section and the second container section adapted to hold between about 0.5 ml to about 10 ml of the first liquid medium and the second liquid medium, respectively. Alternately, the system may include a first container section and a second container section adapted to hold sufficient first liquid medium and second liquid medium, respectively, so that the system is repeatedly usable in disinfecting contact lenses. This form of the present systems may be identified as the bulk or multi-dose form.

In another broad aspect of the present invention, methods for disinfecting a contact lens are provided and comprise contacting a contact lens with a liquid medium containing hydrogen peroxide initially present in an amount effective to disinfect the contact lens and a HPDC, preferably a catalase, and in particular catalase resulting from the action of Aspergillus niger, initially present in an amount effective to destroy at least a major amount, that is at least about 50%, and preferably at least about 70% or about 90%, and more preferably substantially all, of the hydrogen peroxide initially present in the liquid medium. The HPDC acts to effect destruction of hydrogen peroxide upon the formation of the liquid medium. This contacting is effective to disinfect the contact lens. In addition, this single contacting step preferably destroys all the hydrogen peroxide initially present in the liquid medium.

The liquid medium used in the contacting is preferably formed by combining a first liquid medium containing hydrogen peroxide and a second liquid medium containing the HPDC, for example, as present in the systems described herein.

These and other aspects of the present invention will become apparent in the following detailed description, examples and claims, particularly when considered in conjunction with the accompanying drawings in which like parts bear like reference numerals.

BRIEF DESCRIPTION OF THE DRAWINGS

FIG. 1 is a partial front view, in perspective, of a container system including a plurality of unit doses.

FIG. 2 is a cross-sectional view taken generally along line 2—2 of FIG. 1.

FIG. 3 is a partial front view, in perspective of an alternate embodiment of a container system including a plurality of unit doses.

FIG. 4 is a cross-sectional view taken generally along line 4—4 of FIG. 3.

FIG. 5 is a partial front view, in perspective, of an additional embodiment of a container system including a plurality of unit doses.

FIG. 6 is a front perspective view of a further embodiment of a container system including a single unit dose.

FIG. 7 is a front side view, in perspective, of a bulk container system in accordance with the present invention.

FIG. 8 is a cross-sectional view taken generally along line 8—8 of FIG. 7.

FIG. 9 is a front view, partially in cross-section, showing the bulk container system of FIG. 7 dispensing a combined liquid medium.

DETAILED DESCRIPTION OF THE INVENTION

The present invention is of value where hydrogen peroxide is used to disinfect all types of lenses, e.g., contact lenses, which are benefitted by periodical disinfecting. Such lenses may be made of any suitable material or combination of materials and may have any suitable configuration not substantially deleteriously affected by the present compositions or the present methods.

In one aspect, the present invention takes advantage of the discovery that combinations of hydrogen peroxide and HPDC can be used together in a combined liquid medium to achieve both disinfection of a contact lens and destruction of the hydrogen peroxide. Thus, the disinfected contact lens can be removed from this combined liquid medium and placed directly in the eye for safe and comfortable wear.

Any suitable HPDC can be employed provided that it functions as described herein. The amount or concentration of hydrogen peroxide and/or the HPDC may need to be adjusted or controlled to achieve the combination of benefits described herein. For any given HPDC, routine experimentation can be employed to determine whether or not the HPDC is effective in accordance with the present invention and/or how much of the HPDC is needed in accordance with the present invention.

Although any suitable HPDC may be employed, it has been found that particularly useful HPDC's for use in accordance with the present invention are catalases, in particular catalases which have one or more advantageous properties. The presently useful catalases preferably have kinetic properties which facilitate their use in the present invention. Specifically, such useful catalases preferably have an acceptably low rate of causing the destruction of hydrogen peroxide so that the contact lens is disinfected before the hydrogen peroxide is destroyed and/or an acceptably high resistance to oxidation by hydrogen peroxide so that reduced or low amounts of the catalase can be employed in the present invention. The catalases preferably are stable over long periods of time, for example, on the order of about 1 month to about 6 months or longer in containers made of polymeric materials, at low concentrations in liquid aqueous media. Catalases, in particular catalases from other than mammalian sources, such as catalases obtained as the result of the action of microorganisms, which have relatively high pI's, for example, a pI of at least about 5.0, are preferred and have advantages, in particular have enhanced shelf stability, e.g., longer effective shelf life, relative to catalases with relatively low pI's. As used herein, the term "pI" refers to the pH at which any given catalase is neutral. In general, the higher the pI is the more basic the catalase is.

In addition, the catalases useful in the present invention preferably have a substantial degree of stability in the presence of hydrogen peroxide. Such stability is advantageous so that relatively low concentrations of catalase are effective to cause the destruction of at least about 95%, preferably substantially all, of the hydrogen peroxide in the combined liquid medium while the contact lens in the combined liquid medium is disinfected. The stability of a catalase in the presence of hydrogen peroxide is inversely proportional to the rate constant, $k_2$ of the reaction in which the catalase is oxidized by hydrogen peroxide. That is, the lower the $k_2$ of a catalase, the higher the stability of the catalase in the presence of hydrogen peroxide. For example, the $k_2$ for conventional bovine catalase is 8.9 $M^{-1}$ $min^{-1}$ while the $k_2$ for catalase obtained as a result of the action of A. Niger is 0.51 $M^{-1}$ $min^{-1}$, where M is molar concentration and min is minutes. These $k_2$ values are reported in De Luca et al., "Inactivation of an Animal and a Fungal Catalase by Hydrogen Peroxide", Archives of Biochemistry and Biophysics, Vol. 320, No. 1, pp. 129–134, 1995, which is incorporated in its entirely herein by reference.

The presently useful catalases have $k_2$'s of about 2.0 or less, more preferably about 0.75 or less. Consistent with the above-noted De Luca et al. Article, $k_2$ is expressed herein as: $M^{-1}$ $min^{-1}$.

A particularly useful catalase in accordance with the present invention is catalase obtained from the action of Aspergillus niger, more preferably such a catalase having a pI of at least about 5.0. Catalase obtained from the action of Aspergillus niger and sold by NOVO is still more preferred.

In accordance with this aspect of the present invention, systems for disinfecting a contact lens comprise a first container section holding a first liquid medium containing hydrogen peroxide, and a second container section holding a second liquid medium, other than the first liquid medium, containing a HPDC.

The first and second container sections are configured to substantially simultaneously provide the first liquid medium and the second liquid medium to form a combined liquid medium containing an amount of hydrogen peroxide from the first liquid medium effective to disinfect a contact lens contacted with the combined liquid medium and an amount of HPDC from the second liquid medium effective to destroy at least a major amount, and more preferably at least about 95% and still more preferably substantially all, of the hydrogen peroxide in the combined liquid medium.

Methods for disinfecting contact lenses are provided. Such methods comprise contacting a contact lens with a liquid medium containing hydrogen peroxide initially present in an amount effective to disinfect the contact lens and a HPDC initially present in an amount effective to destroy all the hydrogen peroxide initially present in the liquid medium. The HPDC acts to effect the destruction of hydrogen peroxide upon the formation of the liquid medium. This contacting is effective in disinfecting the contact lens.

The amount of HPDC employed is preferably sufficient to destroy all the hydrogen peroxide present in the combined liquid medium in which the HPDC is used. Excess amounts of HPDC may be employed. However, very large excesses of HPDC, for example, more than about 300% of the amount needed to destroy all the hydrogen peroxide present in the combined liquid medium are to be avoided since such excessive amounts of HPDC may cause problems with the disinfected lens and/or with the ability to safely and comfortably wear such disinfected lens. The HPDC, is preferably present, when the HPDC is a catalase, in an amount of about 10 to about 1000, more preferably about 20 to about 800, international units of catalase activity per milliliter of liquid medium. The amount of HPDC employed depends not only on the amount of hydrogen peroxide to be destroyed, but also on the specific HPDC being used and the rate at which the hydrogen peroxide is to be destroyed. For example, in an aqueous solution containing about 3% (w/v) hydrogen peroxide, about 5 to about 200, more preferably about 10 to about 200, international units of catalase activity/per milliliter of combined liquid medium is preferably used if the catalase is obtained by the action of Aspergillus niger.

One important advantage of catalase obtained by the action of Aspergillus niger is an ability to effectively function in destroying hydrogen peroxide at reduced levels or concentrations. This is highly beneficial since the reduced concentration of A. niger catalase allows the hydrogen peroxide sufficient time to disinfect the contact lens while, at the same time, destroying hydrogen peroxide, preferably substantially all of the hydrogen peroxide in the liquid medium. Other catalases, for example, bovine catalase, is used at higher levels in order to destroy all the hydrogen peroxide. However, this destruction occurs relatively rapidly so that the lens may not be disinfected by the hydrogen peroxide before the peroxide is destroyed. Reducing the level of bovine catalase is not effective because such reduced level does not destroy all the hydrogen peroxide in the combined liquid medium.

In the present invention, the hydrogen peroxide is preferably used in the combined liquid medium in a disinfecting amount. A disinfecting amount preferably means such amount as will reduce the microbial burden by one log order in three hours. More preferably, the amount of hydrogen peroxide used is such that the microbial load is reduced by one log order in one hour. Particularly preferred are those amounts which reduce the microbial load by one log order in 10 minutes or less. Aqueous hydrogen peroxide solutions, preferably containing about 0.5% to about 6% or about 8% (w/v) of hydrogen peroxide are very effective as first liquid media in the present invention. These solutions are effective at killing bacteria and fungi and other microorganisms which may be found on contact lenses.

The liquid media used as first and second liquid media in accordance with the present invention are preferably selected to have no substantial detrimental benefit on the lens being treated, and on the wearer of the disinfected lens. The liquid media are constituted to allow, and preferably to even facilitate, contact lens disinfecting. The liquid media are preferably aqueous based, for example, having an osmolality of at least about 200 mOsmol/kg, such as in the range of about 200 to about 400 mOsmol/kg, and preferably are aqueous, substantially isotonic liquid media. Particularly useful aqueous liquid media are those derived from saline, e.g., a conventional saline solution or buffered saline solution. During the disinfecting contacting, it is preferred that the combined aqueous liquid medium have a pH in the range of about 2 or 3 to about 9, more preferably about 3 or higher, for example, to about 10, and still more preferably in the range of about 4 or about 5 to about 8. In particular, after all of the hydrogen peroxide has been destroyed, it is preferred that the combined liquid medium have a pH in the range of about 6 to about 8.

In one useful embodiment, the second liquid medium includes an effective amount of a preservative component, for example, an effective preserving amount of a non-oxidative antimicrobial component. Any suitable preservative component may be employed provided that it functions as a preservative and has no significant detrimental effect on the second liquid medium, the combined liquid medium, the contact lens being treated or the wearer of the treated contact lens. Examples of useful preservative components include, but are not limited to, poly[dimethylimino-2-butene-1,4-diyl] chloride, alpha [4-tris (2-hydroethyl) ammonium-dichloride (available from Onyx Corporation under the trademark Polyquarternium 1®), benzalkonium halides such as benzalkonium chloride, alexidine salts, chlorhexidine salts, hexamethylene biguanimides and their polymers, and the like and mixtures thereof.

The amount of preservative component included in the second liquid medium varies over a relatively wide range depending, for example, on the specific preservative component being employed. Preferably, the amount of preservative component is in the range of about 0.000001% to about 0.001% ($^w/_v$) or more.

The liquid media, e.g., aqueous liquid media, employed preferably include a buffer component which is present in an amount effective to maintain the pH of the liquid medium in the desired range. This buffer component may be present in the liquid medium, e.g., either separately or in combination with one or more of the other presently useful components, e.g., with the hydrogen peroxide or HPDC. Among the suitable buffer components or buffering agents which may be employed are those which are conventionally used in contact lens care products. Examples of useful buffer components include those with carbonate functionalities, bicarbonate functionalities, phosphate functionalities, borate functionalities, and the like and mixtures thereof. The buffers may be alkali metal and alkaline earth metal salts, in particular sodium and potassium.

Further, in order to avoid possible eye irritation, it is preferred that the presently useful combined liquid medium has an osmolality (a measure of tonicity) of at least about 200 mOsmol/kg, preferably in the range of about 200 to about 350 or about 400 mOsmol/kg. In an especially useful embodiment, the osmolality or tonicity of the combined liquid medium substantially corresponds to the tonicity of the fluids of the eye, in particularly the human eye.

Any suitable ophthalmically acceptable tonicity component or components may be employed, provided that such component or components are compatible with the other ingredients of the combined liquid medium and do not have deleterious or toxic properties which could harm the eye. Examples of useful tonicity components include sodium chloride, potassium chloride, mannitol, dextrose, glycerin, propylene glycol and mixtures thereof. In one embodiment, the tonicity component is selected from inorganic salts and mixtures thereof.

The amount of ophthalmically acceptable tonicity component utilized can vary widely. In one embodiment, the tonicity component is preferably present in the combined liquid medium in an amount in the range of about 0.5 to about 0.9% ($^W/_V$) of the combined liquid medium.

One or more additional components can be included in one or more of the present useful liquid media. Such additional component or components are chosen to impart or provide at least one beneficial or desired property to the liquid media. Such additional components may be selected from components which are conventionally used in one or more contact lens care compositions and which do not detrimentally interact with the other components present. Examples of such additional components include cleaning agents, wetting agents, nutrient agents, sequestering agents, viscosity builders, contact lens conditioning agents, colorants, and the like. These additional components may each be included in the combined liquid medium in an amount effective to impart or provide the beneficial or desired property to the combined liquid medium. Such additional components may be included in the presently useful liquid media in amounts similar to the amounts of such components used in other, e.g., conventional, contact lens care products.

Examples of useful sequestering agents include disodium ethylene diamine tetraacetate, alkali metal hexametaphosphate, citric acid, sodium citrate and mixtures thereof.

Examples of useful viscosity builders include hydroxyethyl cellulose, hydroxymethyl cellulose, polyvinyl pyrrolidone, polyvinyl alcohol and mixtures thereof.

In a particularly useful embodiment, one or both of the first and second liquid media further include at least one enzyme effective to remove debris or deposit material from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et al U.S. Reissue Pat. No. 32,672 and Karageozian et al U.S. Pat. No. 3,910,296 are useful in the present invention. These patents are incorporated in their entirety by reference herein. Among the useful enzymes are those selected from proteolytic enzymes, lipases and mixtures thereof. Preferred proteolytic enzymes are those which are substantially free of sulfhydryl groups or disulfide bonds, whose presence may react with the active oxygen in the HPLM to the detriment of the activity of the enzyme. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Aspergillus molds. Within this grouping, the still more preferred enzymes are the derived alkaline proteases generically called subtilisin enzymes. Reference is made to Keay, L., Moser, P. W. and Wildi, B. S., "Proteases of the Genus Bacillus". II. Alkaline Proteases, "Biotechnology& *Bioengineering*", *Vol. XII, pp.* 213–249 (1970, March) and Keay, L. and Moser, P. W., "Differentiation of Alkaline Proteases form Bacillus Species" Biochemical and Biophysical Research Comm., Vol. 34, No. 5, pp. 600–604, (1969).

The subtilisin enzymes are broken down into two sub-classes, subtilisin A and subtilisin B. In the subtilisin A grouping are enzymes derived from such species are *B. subtilis, B. liceniformis* and *B. pumilis*. Organisms in this sub-class produce little or not neutral protease or amylase. The subtilisin B. sub-class is made up of enzymes from such organisms a *B. subtilis, B. subtilis* var. *amylosacchariticus, B. amyloliquefaciens* and *B. subtilis* NRRL B3411. These organisms product neutral proteases and amylases on a level about comparable to their alkaline protease production. One or more enzymes from the subtilisin A sub-class are particularly useful.

In addition other preferred enzymes are, for example, pancreatin, trypsin, collagenase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. this standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

Using the present compositions to disinfect a contact lens may be accomplished by contacting the lens to be disinfected with a liquid medium containing both hydrogen peroxide and a HPDC.

In the event that a debris removing enzyme is present in the composition, the contact lens in the liquid medium is also effectively cleaned of such debris. This cleaning action can occur before the lens is disinfected, at the time the lens is being disinfected, or after the lens is disinfected.

It is preferred that the lens be contacted with, e.g., immersed in, the liquid medium for a time sufficient, more preferably in the range of about 1 minute to about 4 hours and still more preferably in the range of about 5 minutes to about 1 hour, to effectively disinfect the lens. It is also preferred that substantially all of the residual hydrogen peroxide in the liquid medium be destroyed in less than about 3 hours or about 4 hours, more preferably in less than about 1 hour and still more preferably in less than about 30 minutes after the hydrogen peroxide and HPDC are combined.

The disinfecting contacting preferably occurs in a quantity, e.g., about 5 ml to about 15 ml, of the combined liquid medium at a temperature to maintain the liquid medium substantially liquid. It is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs for a time to effectively disinfect the lens being treated.

After this contacting, the disinfected lens is preferably taken from the liquid medium and placed directly in the eye for safe and comfortable wear.

Alternately, the disinfected lens can be rinsed, e.g., with saline solution, to free the lens of enzyme or enzymes prior to placing the disinfected lens into the eye.

Referring now to the drawings, FIG. 1 illustrates a strip of individual side-by-side pairs of pouches, shown generally at 10. Strip 10 includes a series, for example, about 5 to about 10 or more, individual strip sections 12. Each of these strip sections 12 is a component of the strip 10 but can be separated from the other sections along perforations 14.

Each of the sections 12 include a first pouch 16 and a second pouch 18. Each of the first pouches 16 typically include about 3 to about 5 ml of a first liquid medium having a composition of a saline solution containing 6% (w/v) hydrogen peroxide and having a pH of about 3. Each of the second pouches 18 include about 3 to about 5 ml of a second liquid medium containing a buffered aqueous saline solution containing about 160 international units of catalase resulting from the action of A. niger. The second liquid medium includes a sufficiently high buffer concentration so that the combined liquid medium—from one first pouch and one second pouch—has a pH of about 6 to about 8. Each of the first pouches 16 include a first outlet portion 22 while each of the second pouches 18 include a second outlet portion 24. The pouches are sealed along a top perforation 26.

The various components of strip 10 can be made of any suitable polymeric material. Such material or materials should be such as to have no substantial detrimental effect on, and to not be substantially detrimentally affected by, the liquid media present in the first pouches 16 and second pouches 18. Examples of such suitable polymeric material include polyethylene terephthalete, other polyethylene polyesters, low and high density polyethylenes, polypropylene and polyvinylchloride.

Strip 10 is used as follows:

When it is desired to disinfect a pair of contact lenses, they are placed in a conventional contact lens container. One strip section 12 is separated along perforation 14 from the remainder of strip 10. The pouches 16 and 18 of this separated section 12 are unsealed by ripping the top 28 from the remainder of the separated section along top perforation 26. Each of the pouches 16 and 18 is emptied into the lens container. The liquid in the lens container is allowed to contact the contact lenses for about 4 hours. Thereafter, the lenses, which are now disinfected, can be removed from the lens container and placed directed in the eye for safe and comfortable wear. Alternately, the disinfected lenses can be rinsed in a conventional buffered saline solution before being placed in the eye.

Referring now to FIG. 3, an alternate embodiment of the apparatus is shown. In this embodiment, a strip of individual back-to-back pairs of pouches, shown generally as 30, include a series, for example, about 5 to about 10 or more, individual strip sections 32. Each of these strip sections 32 is a component of the strip 30 but can be separated from the other sections along perforations 34.

Each of the sections include a first pouch 36 and a second pouch 38, as shown in FIG. 4. Each of the first pouches 36 is oriented back-to-back with a second pouch 38. In this embodiment, first pouch 36 and second pouch 38 include a common wall 39.

Each of the first pouches 36 include about 3 to about 5 ml of a first liquid medium having a composition identical to the solution as described as being included in first pouch 16. Each of the second pouches 38 include about 3 to about 5 ml of a second liquid medium having a composition identical to the liquid medium in second pouch 18. Each of the pouches 36 and 38 includes an outlet portion 40. The pouches are sealed along a top perforation 46.

The various components of strip 30 can be made of any suitable polymeric material, for example, as described above with regard to strip 10.

When it is desired to disinfect a pair of contact lenses, they are placed in a conventional contact lens container. One strip section 32 is separated along perforation 34 from the remainder of strip 30. The pouches 36 and 38 of the separated strip section 32 are unsealed by ripping off the top 48 along top perforation 46. Each of these pouches 36 and 38 is then emptied into the lens container. The liquid in the lens container is allowed to contact the contact lenses for about 4 hours. Thereafter, the lenses, which are now disinfected, can be removed from the lens container and placed directly in the eye for safe and comfortable wear. Alternately, the disinfected lenses can be rinsed in a conventional buffered saline solution before being placed in the eye.

Referring now to FIG. 5, an additional embodiment of the present system is shown. In this embodiment, a strip of individual side-by-side pairs of pouches, shown generally as 50, includes a series, for example, about 5 to about 10 or more, of individual strip sections 52. The strip 50 shown in FIG. 5 is used in producing the individual sections 52. As part of the manufacturing process, each of the sections 52 is separated from strip 50 along perforations 54. As shown in FIG. 6, the backside 64 of the section 52 is coated with adhesive, the section is folded along fold line 56, and the two pouches 66 and 68 are adhered together. The adhered section 52 is what is actually sold to the consumer. Each of the first pouches 66 includes about 3 to about 5 ml of a first liquid medium having a composition identical to the solution as described as being included in first pouch 16. Each of the second pouches 68 include about 3 to about 5 ml of a second liquid medium having a composition identical to the liquid medium in second pouch 18.

Strip sections 52 are used as follows. When it is desired to disinfect a pair of contact lenses, they are placed in a conventional contact lens container. A strip section 52 is made available. The pouches 66 and 68 are unsealed by ripping the top 70 from the remainder of the strip section 52. This opens the pouches 66 and 68 at the first and second outlet portions 72 and 74, respectively. Each of the pouches 66 and 68 is then emptied into the lens container. The liquid in the lens container is allowed to contact the contact lenses for about 4 hours. Thereafter the lenses, which are now disinfected, can be removed from the lens container and placed directly in the eye for safe and comfortable wear. Alternately, the disinfected lenses can be rinsed in a conventional buffered saline solution before being placed in the eye.

Each of the embodiments shown in FIGS. 1 to 6 involve unit dose increments.

FIGS. 7 to 9 illustrate a further embodiment of the present system in which bulk quantities of the first and second liquid media are provided.

The "single bottle" embodiment of the present system, shown generally at 80 includes a container body 82, a threaded upper portion 84 and an outlet tip portion 86.

The container body 82 includes an outer wall 88 and an inner partition 90 which extends upwardly from the bottom 92 of the container body. An upper partition 94 extends from wall 97 and divides chamber 96 into first portion 98 and second portion 100.

A first container section 93 is provided and is in communication with first portion 98 through first conduit 106. A second container section 95 is provided and is in communication with second portion 100 through second conduit 108. First and second container sections 93 and 95 each has a volume of about 250 ml.

The threaded upper portion 84 is hollow and includes an outer surface 102 which is adapted to engage a threaded bottle cap (not shown) to thereby secure the threaded bottle cap over the outlet tip portion 86 during periods of nonuse of bottle 80.

The outlet tip portion 86 defines an outlet conduit 104 which is in fluid communication with chamber 96.

The various components making up bottle 80 can be made of any suitable polymeric material. Such material or materials should be such as to have no substantial detrimental effect on, and to not be substantially detrimentally affected by, the liquid media present in the first and second container sections 93 and 95. In addition, the body 82 of the bottle 80 should be sufficiently flexible and resilient to be squeezable. Examples of suitable polymeric materials include polyethyleneterephthalate, other polyethylene polyesters, low and high density polyethylenes, polypropylene and polyvinylchloride. As noted above, the container body 82 should be constructed so as to be squeezable by the application of manual force to urge liquid from the first and second container sections 93 and 95 into chamber 96, as will be discussed hereinafter.

First container section 93 is filled with a hydrogen peroxide-containing solution identical to that included in above with regard to first pouch 16. Second container section 95 is filled with a liquid medium identical to that included in second pouch 18.

Bottle 80 is used as follows. When it is desired to disinfect a pair of contact lenses, they are placed in a conventional contact lens container. Bottle 80 is uncapped. Using manual force, container body 82 is squeezed to urge liquid from the first and second container sections 93 and 95 to flow into first and second chamber sections 96 and 100, respectively. The top portion of bottle 80 is sufficiently transparent so that it can be determined how much volume of each liquid is in chamber 96. The squeezing continues until a sufficient amount, for example, about 3 ml to about 5 ml, of each liquid is included in chamber 96. In addition, equal volumes of first and second liquid medium should be present. Upper partition 94 includes an indexing line 110 to aid the user in determining when a sufficient amount of each liquid is present in chamber 96.

After the desired amounts of the two liquids have been placed in chamber 96, bottle 80 is turned upside down without further squeezing. The liquid in chamber 96 is combined and passes out of outlet conduit 104 into the lens container. Thereafter, the bottle 80 is capped and stored. The liquid in the lens container is allowed to contact the contact lenses for about 4 hours. Thereafter, the lenses, which are now disinfected, can be removed from the lens container and placed directly in the eye for safe and comfortable wear. Alternately, the disinfected lenses can be rinsed in a conventional buffered saline solution before being placed in the eye.

The following non-limiting examples illustrate certain aspects of the present invention.

EXAMPLE 1

Quantities of the following two compositions are prepared by blending together the individual ingredients.

| COMPOSITION A |  |
|---|---|
| Hydrogen Peroxide (6% ($^w$/v)) in water at a pH of 3. | |
| COMPOSITION B | |
| Sodium chloride | 1.7% ($^w$/v) |
| Dibasic sodium phosphate heptahydrate | 0.804% ($^w$/v) |
| Monobasic sodium phosphate monohydrate | 0.182% ($^w$/v) |
| Disodium EDTA | 0.2% ($^w$/v) |
| Liquid catalase [1] | 20 International Units/ml |
| Purified water | QS-ad |

[1] Catalase obtained as the result of the action of Aspergillus niger and sold by NOVO. This material includes 35–45% by weight of glycerol and 10% by weight of ethanol. The catalase has a pI of more than 5.0 and a $k_2$ believed to be about 0.5.

EXAMPLE 2

A unit dose of 5 ml of each of the compositions prepared in Example 1 is placed in different pouches 16 and 18 of a strip section 12 as shown in FIG. 1.

EXAMPLE 3

After being maintained at room temperature for two weeks, the strip section 12 of Example 2 is used to disinfect a pair of contact lenses. The lenses are placed in a conventional contact lens holder which is then placed in a conventional vial used to disinfect contact lenses. The strip section 12 is opened and both Composition A and Composition B are simultaneously added to the vial. The contact lenses are immersed in the resulting combined composition.

Approximately 4 hours after the combined composition is formed, the lenses are removed from the vial and holder and are placed directly into the eyes of a human being for safe and comfortable wear. It is found that during the above-noted 4 hour period the contact lenses are disinfected and all the hydrogen peroxide originally present in the vial from Composition A is destroyed.

EXAMPLE 4

Using a two compartment bottle 80 as shown in FIGS. 7 to 9, 250 ml of each of the compositions prepared in Example 1 is placed in a different container section 93 or 95. Composition A is placed in first container section 93 and Composition B is placed in second container section 95.

EXAMPLE 5

After being maintained (in a sealed condition) at ambient temperature for two weeks, the two compartment bottle 80 of Example 4 is used to provide 5 ml of each of Compositions A and B simultaneously to a vial containing a pair of contact lenses to be disinfected (in a holder as in Example 3). The contact lenses are immersed in the resulting combined composition.

Approximately 4 hours after the combined composition is formed, the lenses are removed from the vial and holder and are placed directly into the eyes of a human being for safe and comfortable wear. It is found that during the above-noted 4 hour period the contact lenses are disinfected and all the hydrogen peroxide originally present in the vial from Composition A is destroyed.

EXAMPLE 6

Example 5 is repeated 25 times over a period of two months. In all cases, approximately 4 hours after the combined composition is formed, the lenses are removed from the vial and holder and are placed directly into the eyes of a human being for safe and comfortable wear. Also, in all cases, it is found that after the 4 hour contacting period the contact lenses are disinfected and all the hydrogen peroxide originally present in the vial from Composition A is destroyed.

EXAMPLE 7

Example 1 is repeated except that bovine catalase is used in place of catalase obtained as the result of the action of Aspergillus niger. The bovine catalase has a pI of 6.0–6.5 and a $k_2$ believed to be about 8.9.

Examples 2 and 3 are repeated using the compositions prepared in this Example 7.

After the 4 hour contacting period, it is found that the contact lenses have been disinfected, but a substantial amount (about 30%) of the hydrogen peroxide originally present in the vial when the combined composition is formed remains. A substantial amount of hydrogen peroxide remains even when the contacting period is extended. Because of this residual hydrogen peroxide, it is necessary to rinse the disinfected contact lens with saline before placing the lenses in the eyes of a human being for safe and comfortable wear.

The incomplete destruction of hydrogen peroxide is believed to be the result of the catalase being oxidized by the peroxide too quickly.

EXAMPLE 8

Example 7 is repeated except that catalase obtained as the result of the action of Micrococcus luteus is used in place of bovine catalase. The Micrococcus luteus catalase has a pI of about 4.7.

Substantially similar results to those obtained in Example 7 are observed.

The incomplete destruction of hydrogen peroxide is believed to be the result of the catalase becoming unstable in and/or adhered to the pouch, so that the combined composition has an insufficient amount of active catalase.

EXAMPLE 9

Example 1 is repeated except that bovine catalase in a concentration of 120 International Units/ml is used in place of the catalase obtained as the result of the action of Aspergillus niger. The bovine catalase has a pI of 6.0–6.5 and a $k_2$ of about 8.9.

Examples 2 and 3 are repeated using the compositions prepared in this Example 9.

After the 4 hour contacting period, it is found that all the hydrogen peroxide originally present in the vial when the combined composition was formed is destroyed. However, the contact lenses are not disinfected.

EXAMPLE 10

Example 1 is repeated except that the catalase obtained as the result of the action of Aspergillus niger is that sold by Genencor and has a pI of about 4.7.

Examples 2 and 3 are repeated using the compositions prepared in this Example 10.

After the 4 hour contacting period, it is found that the contact lenses have been disinfected, but a substantial amount (about 30%) of the hydrogen peroxide originally present in the vial when the combined composition is formed remains. A substantial amount of hydrogen peroxide remains even when the contacting period is extended. Because of this residual hydrogen peroxide, it is necessary to rinse the disinfected contact lens with saline before placing the lenses in the eyes of a human being for safe and comfortable wear.

The incomplete destruction of hydrogen peroxide is believed to be the result of the adsorption of the catalase on the pouch over time which is likely due to the relatively low pI of the catalase. Thus, such catalase-containing compositions have relatively short effective shelf lives in such pouches.

EXAMPLE 11

Example 1 is repeated except that the catalase obtained as the result of the action of Aspergillus niger is that sold by CalBioChem and has a pI of about 4.7.

Examples 2 and 3 are repeated using the compositions prepared in this Example 11.

After the 4 hour contacting period, it is found that the contact lenses have been disinfected, but a substantial amount (about 30%) of the hydrogen peroxide originally present in the vial when the combined composition is formed remains. A substantial amount of hydrogen peroxide remains even when the contacting period is extended. Because of this residual hydrogen peroxide, it is necessary to rinse the disinfected contact lens with saline before placing the lenses in the eyes of a human being for safe and comfortable wear.

The incomplete destruction of hydrogen peroxide is believed to be the result of the adsorption of the catalase on the pouch over time which is likely due to the relatively low pI of the catalase.

Examples 7 to 11 illustrate that not all combinations of hydrogen peroxide and catalase are useful to obtain all the advantages of the present invention. Some catalases, such as bovine catalase and Micrococcus luteus catalase, have kinetic and/or one or more other properties which prevent both contact lens disinfection and complete destruction of hydrogen peroxide after simultaneous formation of a combined composition in accordance with the present invention.

On the other hand, catalase obtained as the result of the action of Aspergillus niger, and in particular such catalase having a relatively high pI, has been found to be particularly effective in accordance with the present invention to achieve both contact lens disinfection and complete destruction of residual hydrogen peroxide.

While this invention has been described with respect to various specific examples and embodiments, it is to be understood that the invention is not limited thereto and that it can be variously practiced within the scope of the following claims.

What is claimed is:

1. A system for disinfecting a contact lens comprising:
    a first container section holding a first liquid medium containing hydrogen peroxide;
    a second container section holding a second liquid medium containing liquid catalase having a pI of at least 5.0 and a rate constant, $k_2$ of the reaction in which the catalase is oxidized by hydrogen peroxide of about $2.0\ M^{-1}\ min^{-1}$ or less, where M is molar concentration and min is minutes; and
    said first and second container sections being configured to substantially simultaneously provide said first liquid medium and said second liquid medium to form a combined liquid medium containing an amount of hydrogen peroxide from said first liquid medium effective to disinfect a contact lens contacted with said combined liquid medium and an amount of said liquid catalase from said second liquid medium effective to destroy at least about 95% of the hydrogen peroxide in the combined liquid medium.

2. The system of claim 1 wherein said catalase is present in an amount from said second liquid medium effective to destroy at least 95% of the hydrogen peroxide in the combined liquid medium.

3. The system of claim 2 wherein the amount of said catalase in the combined liquid medium is controlled so that the contact lens in contact with the combined liquid medium is disinfected before at least 95% of the hydrogen peroxide in the combined liquid medium is destroyed.

4. The system of claim 1 wherein the composition of at least one of said first liquid medium and said second liquid medium is controlled so that the contact lens in contact with the combined liquid medium is disinfected before all the hydrogen peroxide in the combined liquid medium is destroyed.

5. The system of claim 3 wherein the composition of at least one of said first liquid medium and said second liquid medium is controlled so that the contact lens in contact with the combined liquid medium is disinfected before all the hydrogen peroxide in the combined liquid medium is destroyed.

6. The system of claim 1 wherein said catalase is catalase obtained as the result of the action of Aspergillus niger.

7. The system of claim 1 wherein said first and second container sections are holding between about 0.5 ml to about 10 ml of said first liquid medium and said second liquid medium, respectively.

8. The system of claim 1 wherein said first and second container sections are holding sufficient said first liquid medium and said second liquid medium, respectively, so that the system is repeatedly usable in disinfecting contact lenses.

9. A system for disinfecting a contact lens comprising:
    a first container section holding a first liquid aqueous medium containing hydrogen peroxide;
    a second container section holding a second liquid aqueous medium containing liquid catalase obtained as the result of the action of Aspergillus niger and having a pI of at least 5.0; and
    said first and second container sections being configured to substantially simultaneously provide said first liquid aqueous medium and said second liquid aqueous medium to form a combined liquid aqueous medium containing an amount of hydrogen peroxide from said first liquid aqueous medium effective to disinfect a contact lens contacted with said combined liquid aqueous medium and an amount of said liquid catalase from said second liquid medium effective to destroy all of the hydrogen peroxide in the combined liquid aqueous medium.

10. The system of claim 9 wherein the composition of at least one of said first liquid aqueous medium and said second liquid aqueous medium is controlled so that the contact lens in contact with the combined liquid aqueous medium is disinfected before all the hydrogen peroxide in the combined liquid aqueous medium is destroyed.

11. The system of claim 9 wherein said first and second container sections are holding between about 0.5 ml to about 10 ml of said first liquid aqueous medium and said second liquid aqueous medium, respectively.

12. The system of claim 9 wherein said first and second container sections are holding sufficient said first liquid aqueous medium and said second liquid aqueous medium, respectively, so that the system is repeatedly usable in disinfecting contact lenses.

13. A method for disinfecting a contact lens comprising:
    substantially simultaneously contacting a contact lens which is to be disinfected with a liquid medium containing both hydrogen peroxide initially present in an amount effective to disinfect said contact lens and liquid catalase having a pI of at least 5.0 and a rate constant, $k_2$, of the reaction in which the catalase is oxidized by hydrogen peroxide of about $2.0\ M^{-1}\ min^{-1}$ or less, where M is molar concentration and min is minutes, said liquid catalase initially present in an amount effective to destroy all the hydrogen peroxide initially present in said liquid medium, said catalase acting to effect the destruction of hydrogen peroxide upon the formation of said liquid medium, thereby disinfecting said contact lens and destroying all the hydrogen peroxide present in said liquid medium.

14. The method of claim 13 which further comprises forming said liquid medium by combining a first liquid medium containing said hydrogen peroxide and a second liquid medium containing said catalase.

15. The method of claim 13 wherein said catalase is catalase obtained as the result of the action of Aspergillus niger.

* * * * *